(12) United States Patent
Areskoug et al.

(10) Patent No.: US 6,486,378 B1
(45) Date of Patent: Nov. 26, 2002

(54) WOUND DRESSING

(75) Inventors: Stefan Areskoug, Molnlycke (SE);
Bengt W. Lindquist, Molndal (SE);
Staffan Kuuse, Hindas (SE)

(73) Assignee: Molnlycke Health Care AB, Gothenburg (SE)

( * ) Notice: Subject to any disclaimer, the term of this patent is extended or adjusted under 35 U.S.C. 154(b) by 0 days.

(21) Appl. No.: 09/914,428

(22) PCT Filed: Feb. 2, 2000

(86) PCT No.: PCT/SE00/00201
§ 371 (c)(1),
(2), (4) Date: Dec. 7, 2001

(87) PCT Pub. No.: WO00/51650
PCT Pub. Date: Sep. 8, 2000

(30) Foreign Application Priority Data

Mar. 1, 1999 (SE) .............................................. 9900737

(51) Int. Cl.7 ................................................ A61F 13/00
(52) U.S. Cl. ............................. 602/41; 602/46; 602/52; 602/53; 602/56

(58) Field of Search ............................... 602/41–43, 46, 602/52–54, 56; 604/358

(56) References Cited

U.S. PATENT DOCUMENTS 4,733,659 A * 3/1988 Edenbaum

FOREIGN PATENT DOCUMENTS

| SE | 456966 | 11/1988 |
|---|---|---|
| WO | WO 96/21682 | 7/1996 |
| WO | WO 97/42985 | 11/1997 |

* cited by examiner

Primary Examiner—Michael A. Brown
Assistant Examiner—Lalita M. Hamilton
(74) Attorney, Agent, or Firm—Young & Thompson

(57) ABSTRACT

A wound dressing includes an hydrophilic foam layer which is coated with a liquid-permeabe adhesive layer on one side. The dressing includes an absorbent layer disposed on the foam layer on the side opposite to the adhesive coating, wherein absorbent layer is able to drain the foam layer through the action of capillary forces, and wherein the dressing further includes elements that ensure effective contact between the absorbent layer and the foam layer.

4 Claims, 2 Drawing Sheets

WOUND DRESSING

FIELD OF INVENTION

The present invention relates to a wound dressing that includes an hydrophilic foam layer that is covered on one side with a liquid permeable adhesive layer.

BACKGROUND OF THE INVENTION

Weeping wounds or sores are typically treated with wound dressings that include a pad which absorbs surplus fluid exuding from the wound. The fluid, or semifluid, absorbed by the pad spreads laterally in the dressing and may reach the skin which lies around the edges of the wound and which then comes into contact with the fluid. This fluid contact is potentially harmful to the skin, as it may result in maceration of the skin or damage the skin in some other way. This is a highly common complication in the treatment chronic wounds and sores.

Another problem is that the change of dressings will often have a deleterious affect on the healing process.

An object of the present invention is to provide a wound dressing with which the risk of skin maceration is reduced and with which that part of the wound pad that lies proximal to the wound is kept free from fluid until the pad becomes saturated. Another object of the invention is to provide a two-layer dressing that includes a drainable first layer of hydrophilic foam that lies nearest the wound. This layer can be left on the wound, or sore, over a long period of time whereas a second layer that functions to drain the first layer can be changed at regular intervals.

SUMMARY OF THE INVENTION

These objects are achieved with a wound dressing which comprises an hydrophilic foam layer that is coated with a layer of liquid-permeable adhesive on one side, wherein the dressing is characterized by an absorbent layer disposed on the foam layer on the opposite side of the adhesive coating and which has the ability to drain the foam layer by capillary action; and in that the dressing includes means for ensuring that good contact is obtained between the absorbent layer and the foam layer. The capillary forces in the layer of absorbent material act to empty the foam layer of fluid, therewith essentially eliminating the risk of skin maceration. This enables the foam layer to remain on the wound bed for a longer period of time without needing to be chanced.

In one preferred embodiment of the invention, the hydrophilic foam layer has a maximum thickness of 2 mm and a mean cell size of 300–500 $\mu$m. The adhesive coating is comprised of a soft, sticky, hydrophobic elastomer.

The invention also relates to a wound dressing intended for co-action with an absorbent body, wherein the dressing is characterized by an hydrophilic foam layer which has on one side an adhesive coating that extends over the whole of its surface without blocking or clogging the pores of said layer, wherein said layer has a thickness of at most 2 mm and a mean cell size of 300–500 $\mu$m.

BRIEF DESCRIPTION OF THE DRAWINGS

The invention will now be described with reference to the accompanying drawings, in which.

DESCRIPTION OF EMBODIMENTS

Figures 1, 1A:
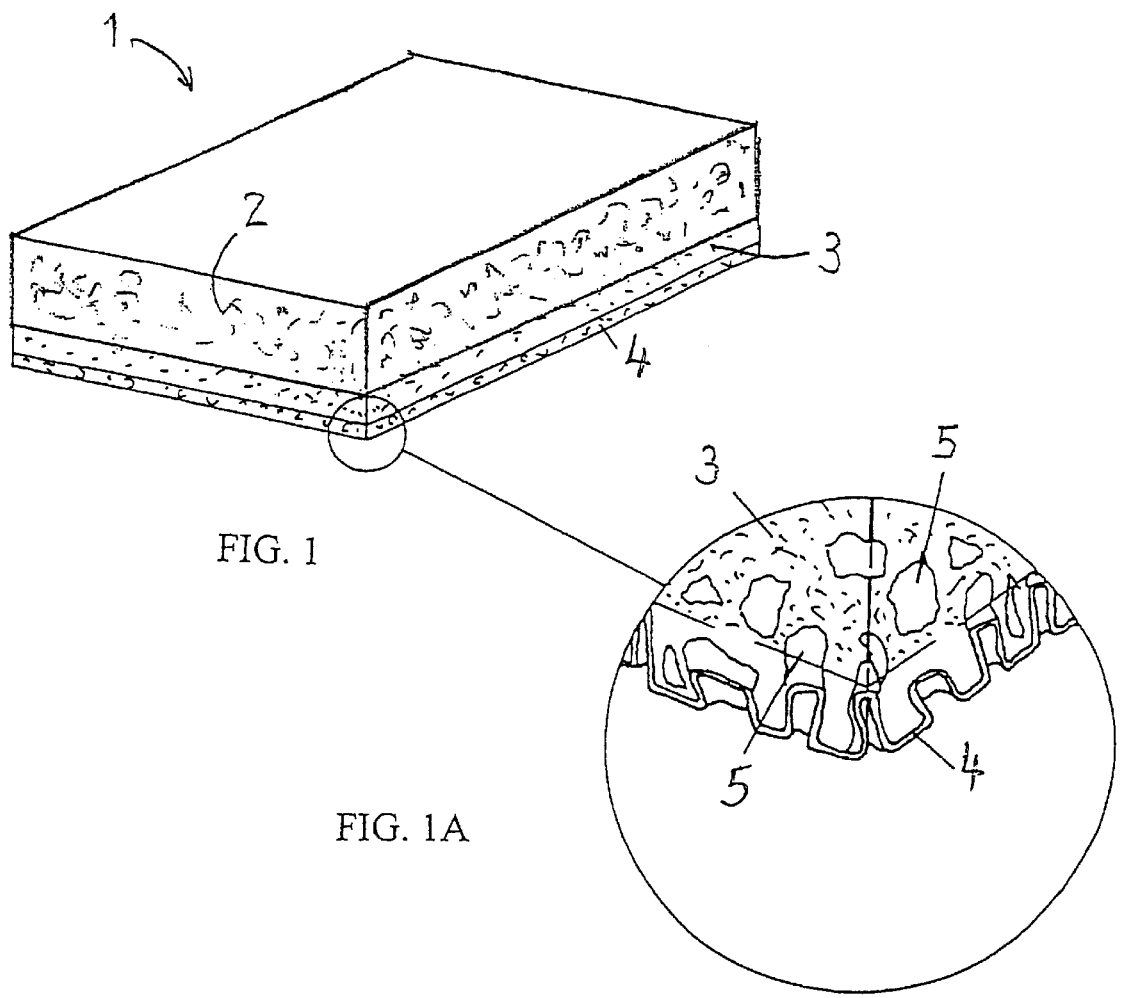
FIG. 1 is a schematic perspective view of a part of a wound dressing according to a first embodiment of the invention.
FIG. 1A shows part of the dressing in FIG. 1 in larger scale.

The wound dressing illustrated in FIG. 1 includes a wound pad 1 that comprises two layers 2, 3. The bottom layer 3 is comprised of an hydrophilic polyurethane foam having open cells. The underside of the foam layer, which faces towards the wound when worn, is provided with a coating 4 of soft, sticky, hydrophobic elastomeric material, preferably silica gel. As illustrated schematically in FIG. 1A, the gel layer is disposed so that part of the walls of the open cells or pores 5 of the foam material that open onto the gel coated side will also be coated with gel. Because the gel layer 3 does not close the pores, but merely covers a part of the walls of some of the pores of the foam facing towards the wound, excess wound fluid or exudate is drawn up into the foam material and absorbed therein. A method of producing such a gel layer is described in WO 97742985 A1, to which reference is made for a closer understanding of the method of manufacture. The upper layer 2 is comprised of an absorbent material that is able to drain the bottom layer 3, in other words the capillary forces in the upper material shall be greater than the capillary forces in the bottom layer. When the upper layer is comprised of foam material, the pores in the upper layer shall be smaller than the pores in the bottom layer. When the upper layer is comprised of fibrous material, the capillaries in the material may be so narrow that the capillary forces will be greater in this layer than in the bottom layer. The size of the capillaries of fibrous material can generally be reduced by compression, and it is therefore relatively easy to produce fibrous material that is able to drain the foam layer 3.

The layer 2 may be comprised of cellulose fluff, although other material may be used, such as gauze or non-woven material.

When such a dressing is placed over a weeping wound or sore, surplus fluid or exudate from the sore will be drawn up into the layer 3. As the exudate drawn into the layer 3 comes into contact with the upper layer 2 it will be transported through the layer 3 and absorbed in the layer 2 before being able to spread in the layer 3 to any appreciable extent, by virtue of the capillary forces acting in the layer 2 being greater than the capillary forces acting in the layer 3. Fluid exuded from the wound will therefore be absorbed in the upper layer 2 until said layer is saturated, and not in the bottom layer 3. This essentially eliminates the risk of long term contact of wound fluid with the skin around the edges of the wound such as to cause maceration of the skin. However, the bottom layer 3 will still remain moist, so as to sustain a desirable moist wound environment. The bottom layer 3 will not be filled with fluid until the upper layer is saturated. The upper layer will therefore preferably be dimensioned to accommodate all or at least the largest part of the fluid that is intended to be absorbed by the dressing, so that the bottom layer can be drained during the full life time of the dressing. The bottom layer 3 shall therefore have a thickness which positively distances absorbed exudate from the wound bed while, at the same time, being sufficiently thin to ensure that exudate will come into contact with the upper drainage layer 2 as soon as possible. The bottom layer 3 will preferably have a thickness of between 1–2 mm.

The layers 2 and 3 are held together in some suitable way, for instance by means of a support bandage or an elastic tape or plaster, such as to be anchored to that part of the wearer's body on which the wound is situated. In order for the capillary forces in the upper layer 2 to function in the intended manner, it is important that the layers 2 and 3 are in effective contact with each other and that the support bandage is preferably applied so as to press the layer 2 against the layer 3 with only a small force.

Figure 2:
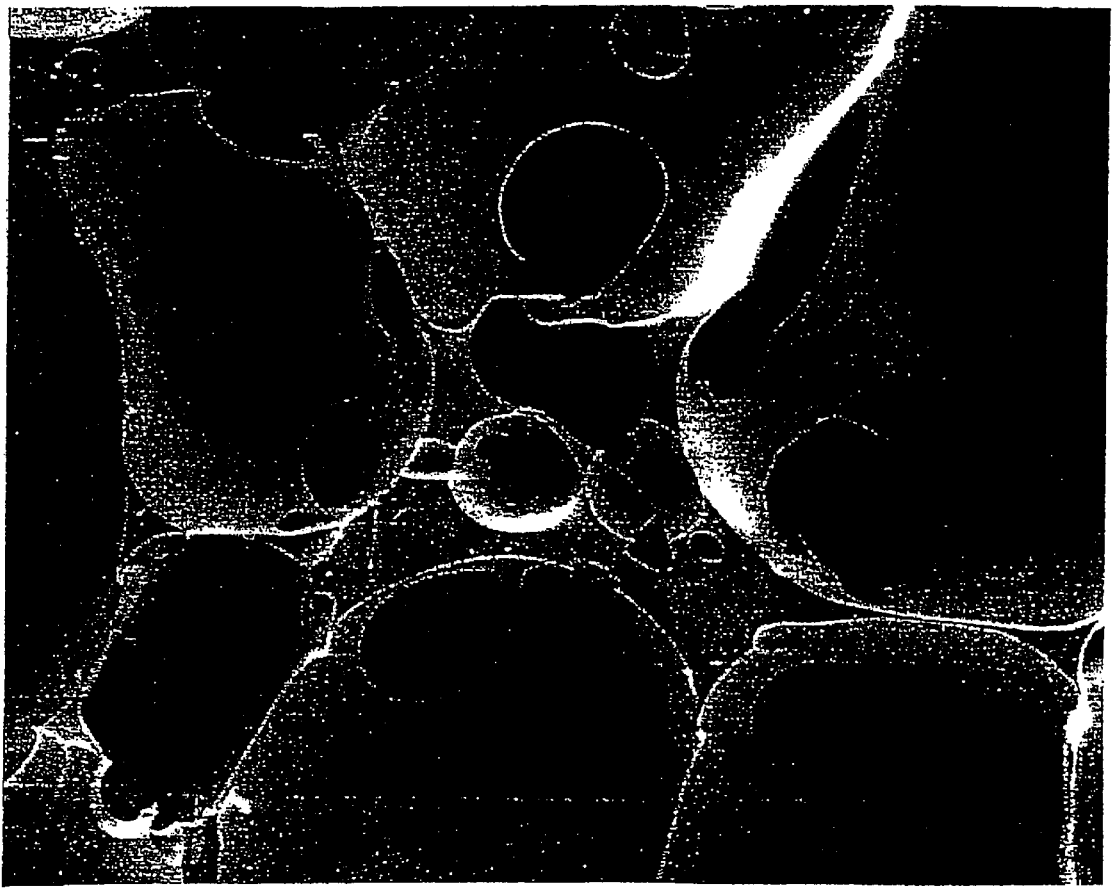
FIG. 2 is an electron microscope image of the pore structure in the absorbent foam material included in the wound dressing of FIG. 1.

The bottom layer is preferably made of a foam material of the kind at present used in wound dressings, for instance a polyurethane foam Amrel LO562-6 from Rynel, USA, in which . . . % of the pores have a size that is greater than . . . $\mu$m. The capillary forces of such foam material are so small as to enable all types of fibrous absorbent bodies at present used in wound care to be able to drain such a layer. FIG. 2 is an electron microscope image of the pore structure of one such material.

The foam layer 3 is particularly flexible and will adapt to the shapes of all parts of a wearer's body on which they can need to be used. Such layers are therefore particularly suitable for use on large wound surfaces and can be left on the wound for the full duration of the healing process. Absorbent bodies comprised of fibrous material are less flexible than bodies of absorbent foam material, and consequently it may be necessary to supplement an inventive gel-coated layer that covers a large wound with several mutually adjacent absorbent bodies of fibrous material in order to ensure that the two layers of the inventive dressing are in effective contact with each other over the whole area of the wound.

It will be understood that the described embodiment can be modified in several ways within the scope of the invention, particularly with respect to the material used in the dressing. For instance, the plastic foam layer may be comprised of other plastic foams, e.g. viscous foam, EVA-foam, silicon foams that have been made hydrophilic, and so on. Also other absorbent fibrous materials may be used, wherewith the fiber body may be given different capillary sizes by appropriate compression of the material. The invention is therefore restricted solely by the contents of the following claims.

What is claimed is:

1. A wound dressing comprising:

an hydrophilic foam layer;

a liquid-permeable adhesive coating on one side of the foam layer; and an absorbent layer disposed on the foam layer on the side opposite to the adhesive coating, wherein said absorbent layer is able to drain the foam layer through the action of capillary forces, and further comprising means that ensure a good contact between the absorbent layer and the foam layer, wherein the hydrophilic foam layer has a thickness of 2 mm at the most and the cells in the foam layer have a mean size of 300–500 $\mu$m.

2. The wound dressing according to claim 1, wherein the adhesive coating is comprised of a soft, tacky, hydrophobic elastomer.

3. The wound dressing according to claim 2, wherein the layer of absorbent material consists of one or more absorbent bodies of fibre material.

4. The wound dressing according to claim 1, wherein the layer of absorbent material consists of one or more absorbent bodies of fibre material.

* * * * *